(12) United States Patent
Wongmahasirikun et al.

(10) Patent No.: US 10,934,243 B2
(45) Date of Patent: Mar. 2, 2021

(54) CATALYST COMPOSITION FOR A PRODUCING PROCESS OF AN UNSATURATED CARBOXYLIC ACID SALT AND ITS DERIVATIVES FROM CARBON DIOXIDE AND OLEFIN

(71) Applicant: PTT GLOBAL CHEMICAL PUBLIC COMPANY LIMITED, Chatuchak (TH)

(72) Inventors: Phonpimon Wongmahasirikun, Bangchak (TH); Sucheewin Chotchatchawankul, Ram Inthra (TH); Khamphee Phomphrai, Klongkum (TH); Sophon Kaeothip, Chatuchak (TH)

(73) Assignee: PTT GLOBAL CHEMICAL PUBLIC COMPANY LIMITED, Chatuchak (TH)

(*) Notice: Subject to any disclaimer, the term of this patent is extended or adjusted under 35 U.S.C. 154(b) by 0 days.

(21) Appl. No.: 16/768,196

(22) PCT Filed: Nov. 23, 2018

(86) PCT No.: PCT/TH2018/000053
§ 371 (c)(1),
(2) Date: May 29, 2020

(87) PCT Pub. No.: WO2019/132784
PCT Pub. Date: Jul. 4, 2019

(65) Prior Publication Data
US 2020/0317598 A1    Oct. 8, 2020

(30) Foreign Application Priority Data
Dec. 25, 2017    (TH) ................................ 1701007764

(51) Int. Cl.
*C07C 57/03* (2006.01)
*B01J 31/22* (2006.01)

(52) U.S. Cl.
CPC .......... *C07C 57/03* (2013.01); *B01J 31/2217* (2013.01); *B01J 2231/40* (2013.01); *B01J 2531/824* (2013.01)

(58) Field of Classification Search
CPC .............. B01J 2231/40; B01J 2531/824; B01J 31/2217; C07C 57/03; C07D 309/32
See application file for complete search history.

(56) References Cited

U.S. PATENT DOCUMENTS

2017/0107166 A1 * 4/2017 Limbach ................. C07C 51/15

FOREIGN PATENT DOCUMENTS

CN    103254408    *  8/2013

OTHER PUBLICATIONS

CN103254408 translated (Year: 2013).*

* cited by examiner

Primary Examiner — Clinton A Brooks
Assistant Examiner — Blaine G Doletski
(74) Attorney, Agent, or Firm — Bond, Schoeneck & King, PLLC; Joseph Noto

(57) ABSTRACT

This invention relates to a catalyst composition for a producing process of an unsaturated carboxylic acid salt and its derivatives from carbon dioxide and olefin, wherein the catalyst composition in the present invention has been proved to be effective in catalyzing the carboxylation of carbon dioxide and olefin, wherein said catalyst composition comprises:
a) a palladium metal complex as shown in structure (I);

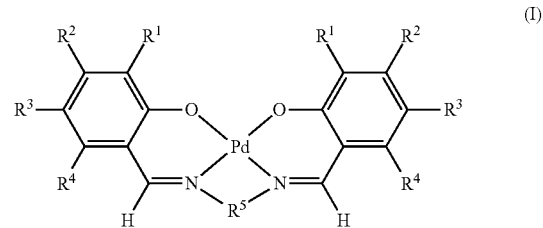

wherein,
$R^1$, $R^2$, $R^3$, and $R^4$ independently represents a group selected from hydrogen atom, halogen atom, alkyl group, alkyl halide group, alkoxy group, amine group, optionally from alkenyl group, alkynyl group, phenyl group, benzyl group, or cylic hydrocarbon group comprising hetero atom;
$R^5$ represents group selected from alkyl group or phenyl group;
b) a ligand selected from organophosphorus compound;
c) a base selected from sodium tert-butoxide, sodium isopropoxide, sodium 2,6-dimethylphenolate, sodium 2,6-difluorophenolate, sodium 2-methylphenolate, or sodium 2-fluorophenol); and
d) a reducing agent.

22 Claims, No Drawings

CATALYST COMPOSITION FOR A PRODUCING PROCESS OF AN UNSATURATED CARBOXYLIC ACID SALT AND ITS DERIVATIVES FROM CARBON DIOXIDE AND OLEFIN

REFERENCE TO RELATED APPLICATION

This application is a U.S. National Phase filing of International Application No. PCT/TH2018/000053, filed Nov. 23, 2018, which relates and claims priority Application No. 1701007764, filed in Thailand on Dec. 25, 2017, the entirety of each of which are hereby incorporated by reference in their entirety.

TECHNICAL FIELD

Chemistry relates to a catalyst composition for a producing process of the unsaturated carboxylic acid salt and its derivatives from carbon dioxide and olefin.

BACKGROUND ART

Carbon dioxide gas is one of the greenhouse gases which is the main factor of global warming causing an environmental problem affected largely to human. Carbon dioxide in atmosphere generated from both natural and human. From the analysis results of Carbon Dioxide Information Analysis Center, about 29.17 thousands million tons of carbon dioxide by mass of carbon was released into atmosphere in 2010 generated from petroleum energy and cement production. It was 4.9% higher than in 2009. This tremendous amount of carbon dioxide affects the global surface temperature at least 2 times higher than other gases together.

It is well known that carbon dioxide is one of the important natural resources because carbon dioxide can be used as raw material in production process of fuel and chemicals. Said used carbon dioxide is renewable resource. However, the main problem of the usage of carbon dioxide is its inert property toward chemical reactions so that it is required a high reactivity substance or catalyst in order to transform carbon dioxide into desired products.

Carbon dioxide has been used as precursor in the production process of desired chemicals such as the precursor in the production of the unsaturated carboxylic acid salt, especially the acrylic acid salt and its derivatives, which further used as precursor in the synthesis of acrylate polymer. Said acrylate polymer can be applied to many applications.

Normally, the unsaturated carboxylic acid salt and its derivatives can be produced from carboxylation of carbon dioxide and small molecule olefins. The products obtained from this process are cheap and can be produced in large amount in petrochemical industry. Although carbon dioxide is one of the optional for a preparation of sodium acrylate and its derivatives in order to produce acrylate polymer for a long time, the usage of olefins in this process has been used for less than 10 years.

Chemistry—A European Journal (2012) discloses the production of sodium acrylate from carbon dioxide and ethylene by catalyzed reaction of bis(cyclooctadiene)nickel, $Ni(COD)_2$), and strong base via deprotonation of nickelalactone to produce π-complex of stable acrylate salt with TON at 10.2.

WO2013098772 and US20130172616 disclose the synthesis of sodium acrylate from the reactions of transition metal-alkene complex and carbon dioxide, followed by the reaction with base and alkene, wherein the catalyst composition comprises bis(cyclooctadiene)nickel, $Ni(COD)_2$), reducing agent, ligand in phosphorous group, and carbine, base, and solvent. The TON obtained was 10.

Chemistry—A European Journal (2014) and patent document WO2015173276 disclose the use of bis(cyclooctadiene)nickel in the synthesis of the unsaturated carboxylic acid salt from ethylene or butadiene by varying the precursors. It was found that base and solvent played important roles in yield production. Sodium 2-fluorophenolate was the best base (TON less than 116) but it is necessary to use (R,R)-(+)-1,2-Bis(di-t-butylmethylphosphino)benzene as the ligand for this reactions.

Chemical Communications (2015) discloses the reaction of carbon dioxide and alkene using dichloro(1,5-cyclooctadiene)palladium(II), $(COD)PdCl_2$) as the catalyst in the synthesis of sodium acrylate and its derivatives (TON less than 29) using Zn(0) as the reducing agent to transform Pd(II) to Pd(0) in catalytic cycle with bis(dicyclohexylphosphino)ethane.

European Journal of Organic Chemistry (2015) and patent document WO2015173277 disclose the catalyst compositions comprising tetrakis(triphenylphosphine)palladium(0) and bis(dicyclohexylphosphino)ethane as the main compositions. It was found that the said catalytic system yield sodium acrylate at TON of 106.

ChemCatChem (2017) discloses the synthesis of sodium acrylate in high boiling point solvent such as N-cyclohexylpyrrolidone, while increasing the pressure of carbon dioxide. It was found that the efficiency of the preparation of sodium acrylate is increase at TON of 514.

WO2015173295 discloses the synthesis of sodium acrylate using transition metal complex fixed on solid support such as silica or crosslinked polystyrene including base and solvent at different temperatures, times, and pressures of ethylene and carbon dioxide as co-components.

WO2015173296 discloses the synthesis of sodium acrylate using base fixed on solid support such as silica or crosslinked polystyrene with bis(cyclooctadiene)nickel (Ni $(COD)_2$), bis(dicyclohexylphosphino)ethane, base, and solvent at different temperatures, times, and pressures of ethylene and carbon dioxide as co-components. TON was found to be 1.1.

Patent document WO2015173307A1 discloses the synthesis of sodium acrylate using tertiary amines and phosphazene as bases, and bis(cyclooctadiene)nickel $(Ni(COD)_2)$, bis(dicyclohexylphosphino)ethane, and tetrahydrofuran (THF) as solvents at different temperatures, times, and pressures of ethylene and carbon dioxide as co-components. TON was found to be 18.8.

US20160229782 disclose the synthesis of acrylic acid and its derivatives using treated solid oxide for acrylate elimination from nickelalactone at different temperatures, times, and pressures as co-components. TON was found to be 1.81.

However, the catalyst for the production process of the unsaturated carboxylic acid salt and its derivatives from carbon dioxide and olefin disclosed so far is limited to the palladium complex and ligands in group of cyclooctadiene or triphenylphosphine only. These substances have not been improved in their structures in order to increase their catalytic abilities.

Moreover, palladium compounds and triphenylphosphine ligand are expensive, air sensitive, and needed to be kept at low temperature (bis(cyclooctadiene)nickel $(Ni(COD)_2)$=2-8° C. and tetrakis(triphenylphosphine)palladium(0), $Pd(PPh_3)_4$)=−20° C.), causing limits in the application at normal condition. Moreover, palladium compounds and ligands in a group of triphenylphosphine or cyclooctadiene ligand such as dichloro(1,5-cyclooctadiene)palladium(II), (COD)PdCl$_2$), and tetrakis(triphenylphosphine)palladium (Pd(PPh$_3$)$_4$) are very expensive, causing limits in the large applications in industrial scale.

From all above reasons, the present invention aims to prepare the catalyst composition for a producing process of the unsaturated carboxylic acid salt and its derivatives having working stability under normal condition, low air sensitive, cheap, and high efficiency.

SUMMARY OF INVENTION

This invention relates to a catalyst composition for a producing process of the unsaturated carboxylic acid salt and its derivatives from carbon dioxide and olefin, wherein this catalyst composition can catalyze carboxylation effectively, wherein said catalyst composition comprises:

a) a palladium metal complex as shown in structure (I);

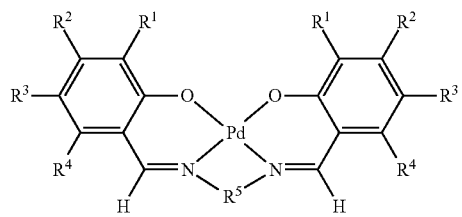

(I)

wherein, $R^1$, $R^2$, $R^3$, and $R^4$ independently represents a group selected from hydrogen atom, halogen atom, alkyl group, alkyl halide group, alkoxy group, amine group, optionally from alkenyl group, alkynyl group, phenyl group, benzyl group, or cylic hydrocarbon group comprising hetero atom;

$R^5$ represents group selected from as alkyl group or phenyl group;

b) a ligand selected from organophosphorus compound;

c) a base selected from sodium tert-butoxide, sodium isopropoxide, sodium 2,6-dimethylphenolate, sodium 2,6-difluorophenolate, sodium 2-methylphenolate, or sodium 2-fluorophenolate); and d) a reducing agent.

DESCRIPTION OF THE INVENTION

The present invention relates to the catalyst composition for a producing process of the unsaturated carboxylic acid salt and its derivatives from carbon dioxide and olefin, wherein the catalyst composition according to this invention is efficiently catalyze the production process of unsaturated carboxylic acid salt and its derivatives. Moreover, the catalyst composition according to the invention is easily synthesized from cheap precursors, stable to air and humid, wherein the catalyst composition according to the invention will be described according to the following description of the invention.

Any aspect showed herein is meant to include its application to other aspects of this invention unless stated otherwise.

Technical terms or scientific terms used herein have definitions as by an ordinary person skilled in the art unless stated otherwise.

Any tools, equipment, methods, or chemicals named here mean tools, equipment, methods, or chemicals being used commonly by an ordinary person skilled in the art unless stated otherwise that they are tools, equipment, methods, or chemicals specific only in this invention.

Use of singular noun or singular pronoun with "comprising" in claims or specification means "one" and including "one or more", "at least one", and "one or more than one".

All compositions and/or methods disclosed and claims in this application aim to cover embodiments from any action, performance, modification, or adjustment without any experiment that significantly different from this invention, and obtain with the objection to utility and resulted as same as the present embodiment according to an ordinary person ordinary skilled in the art although without specifically stated in claims. Therefore, substitutable or similar object to the present embodiment, including any little modification or adjustment that clearly seen by an ordinary person skilled in the art should be construed as remains in spirit, scope, and concept of invention as appeared in appended claims.

Throughout this application, term "about" means any number that appeared or showed here that could be varied or deviated from any error of equipment, method, or personal using said equipment or method.

Hereafter, invention embodiments are shown without any purpose to limit any scope of the invention.

This invention relates to the catalyst composition for a producing process of the unsaturated carboxylic acid salt and its derivatives from carbon dioxide and olefin, wherein the said catalyst composition comprises:

a) a palladium metal complex as shown in structure (I);

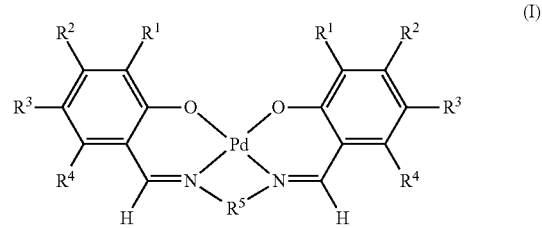

(I)

wherein, $R^1$, $R^2$, $R^3$, and $R^4$ independently represents a group selected from hydrogen atom, halogen atom, alkyl group, alkyl halide group, alkoxy group, amine group, optionally from alkenyl group, alkynyl group, phenyl group, benzyl group, or cylic hydrocarbon group comprising hetero atom;

$R^5$ represents group selected from as alkyl group or phenyl group;

b) a ligand selected from organophosphorus compound;

c) a base selected from sodium tert-butoxide, sodium isopropoxide, sodium 2,6-dimethylphenolate, sodium 2,6-difluorophenolate, sodium 2-methylphenolate, or sodium 2-fluorophenolate); and d) a reducing agent, selected from zinc, L-ascorbic acid, or sodium citrate.

In one embodiment, the palladium metal complex in a) comprises $R^1$, $R^2$, $R^3$, and $R^4$ independently represents group selected from hydrogen atom, halogen atom, alkyl halide group, alkyl group having 1-4 carbon atoms, alkoxy group having 1-4 carbon atoms, or secondary amine with a general formula NRZ wherein $R^6$ represents alkyl group having 1-4 carbon atoms.

In one embodiment, the palladium metal complex in a) comprises $R^1$, $R^2$, $R^3$, and $R^4$ independently represents group selected from, but not limited to hydrogen atom, chlorine atom, tert-butyl group, methoxy group, trifluoromethyl group, or diethylamine group.

In one embodiment, the palladium metal complex in a) comprising R⁵ is selected from, but not limited to alkyl group or phenyl group, wherein R⁵ represents alkyl group selected from, but not limited to ethylene, 1,2-phenylene, binaphthyl, or 1,2-cyclohexyl.

In one embodiment, the palladium metal complex in a) is selected from the palladium metal complex as shown in structure (II), (III), (IV), (V), (VI), or (VIII);

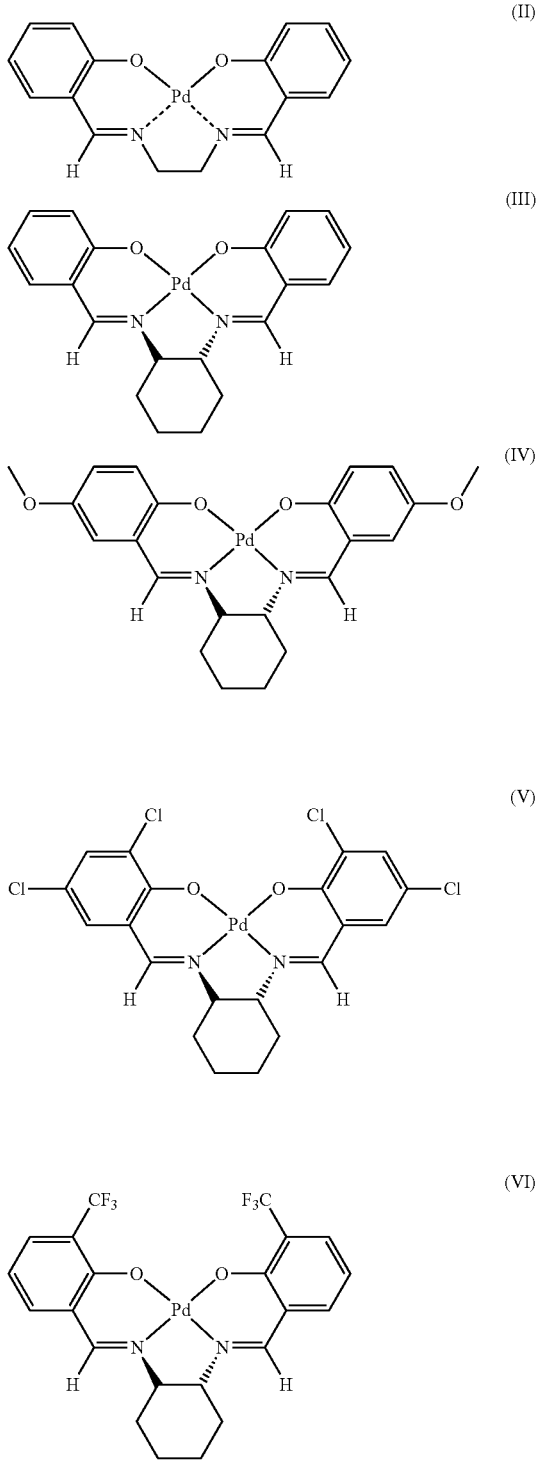

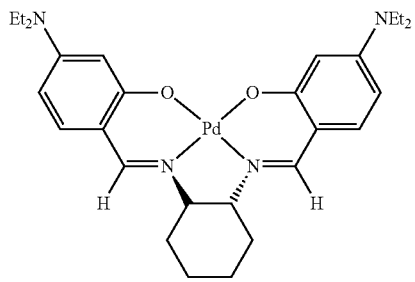

In one embodiment, the palladium metal precursor is selected from, but not limited to palladium chloride ($PdCl_2$), palladium bromide ($PdBr_2$), palladium trifluoroacetate (Pd$(TFA)_2$), or palladium acetate (Pd$(OAc)_2$), preferably palladium acetate.

In one embodiment, the organophosphorus compound in b) is selected from diphosphine group with a general formula $PR^7{}_3CH_2CH_2PR^7{}_3$, wherein $R^7$ is selected from alkyl group, phenyl group, or cycloalkyl group.

In one embodiment, the organophosphorus compound in diphosphine group is selected from, but not limited to bis(dicyclohexylphosphino)ethane, (S, S',R,R')-TangPhos, (R,R)-(−)-2,3-bis(tert-butylmethylphosphino)quinoxaline, (1R,1'R,2S,2'S)-DuanPhos, and (−)-1,2-bis [(2R,5R)-2,5-dimethylphospholano]benzene, preferably bis(dicyclohexylphosphino)ethane.

In one embodiment, the base in c) is selected from, but not limited to sodium tert-butoxide, sodium isopropoxide, sodium 2,6-dimethylphenolate, sodium 2,6-difluorophenolate, sodium 2-methylphenolate, or sodium 2-fluorophenolate, preferable is sodium tert-butoxide or sodium 2-fluorophenolate, most preferable is sodium tert-butoxide.

In one embodiment, the reducing agent in d) is selected from, but not limited to zinc, L-ascorbic acid, or sodium citrate, preferably zinc and sodium citrate, most preferably zinc.

In one embodiment, said catalyst further comprises additive selected from phosphorus compound with a general formula $PR_3{}^8$ wherein $R^8$ is selected from alkoxy group, cycloalkyl group, aryl group, or alkoxy aryl group.

In one embodiment, the additive is selected from, but not limited to triphenylphosphine, tricyclohexylphosphine, tris(2-methoxyphenyl)phosphine, tris(4-methoxyphenyl)phosphine, tris(2,6-dimethoxyphenyl)phosphine), tristearyl phosphite, triphenyl phosphite, tris(2,4-di-tert-butylphenyl) phosphite, tri-p-tolyl phosphite, or the mixture thereof, preferably triphenylphosphine or tristearyl phosphite.

In one embodiment, the mole ratio of the catalyst composition comprising:
a) 1 part of the palladium metal complex;
b) from 0.5 to 2 parts of ligand;
c) from 50 to 400 parts of base; and
d) from 50 to 500 parts of reducing agent.

In one embodiment, this invention relates to the producing process of the unsaturated carboxylic acid salt and its derivatives from carbon dioxide and olefin comprises:
a) adding of the catalyst composition according to any one of claims 1 to 16 in the solvent into the reactor; and
b) condensing olefin and carbon dioxide with mixture obtained from step a) in the reactor;
then, rising the temperature from 100 to 180° C., and heated for 10-25 hours, wherein the mole ratio of olefin to carbon dioxide is from 1 to 2 to 1 to 4.

Preferably, the producing process of the unsaturated carboxylic acid salt and its derivatives from carbon dioxide and olefin comprises:

a) adding of the catalyst composition according to any one of claims 1 to 16 in the solvent into the reactor; and b) condensing olefin and carbon dioxide with mixture obtained from step a) in the reactor. Then, rising the temperature from 130 to 150° C. and heated for 50-25 hours, wherein the mole ratio of olefin to carbon dioxide is from 1 to 4.

In one embodiment, olefin is selected from, but not limited to ethylene, 1,3-butadiene, or 1-hexene.

In each step of the producing process of the unsaturated carboxylic acid salt and its derivatives according to the invention, unless being stated otherwise, the organic solvent may be selected from, but not limited to tetrahydrofuran, anisole, N-cyclohexyl-2-pyrrolidone, phenyl butyl ether, dibutyl glycol ether, dibutyl ether, N,N-dimethylacetamide, N,N-dimethylformamide, N,N-dibutylformamide, or the mixture thereof.

The producing process of the unsaturated carboxylic acid salt and its derivatives according to this invention further comprises the step of drying if needed. Said step is selected from, but not limited to stirring evaporation, vacuum drying, etc.

In one embodiment, the producing process of the unsaturated carboxylic acid salt and its derivatives according to this invention may be operated in the reactor, but not limited to fixed-bed reactor, batch reactor or continuous reactor.

The following examples are for demonstrating of the embodiments of this invention only, not for limitation of the scope of this invention in any way.

Synthesis of Palladium Complex Catalyst

Synthesis of Complex Compound (II)

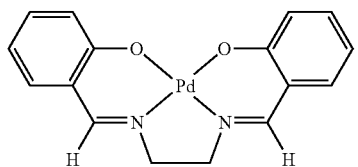

(II)

Palladium acetate (0.89 mmol) was dissolved in hot methanol solvent. Then, N,N'-bis(salicylidene)ethylenediamine (0.89 mmol) in acetone solvent was added and stirred overnight. The obtained suspension was filtered and washed with acetone solvent. The dried yellow powder complex compound was obtained.

Synthesis of Complex Compound (III)

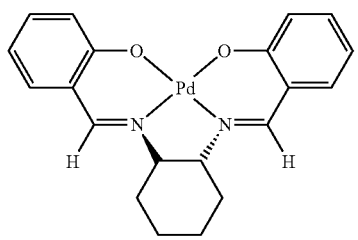

(III)

Palladium acetate (0.89 mmol) was dissolved in hot methanol solvent. Then, (S,S)-(+)-N,N'-bis(salicylidene)-1,2-cyclohexanediamine (0.89 mmol) in acetone solvent was added and stirred overnight. The obtained suspension was filtered and washed with acetone solvent. The dried green powder complex compound was obtained.

Synthesis of Complex Compound (IV)

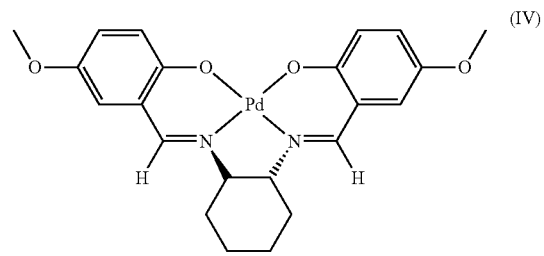

(IV)

Palladium acetate (1.34 mmol) was dissolved in hot methanol solvent. Then, (S,S)-(+)-N,N'-bis(5-methoxylsalicylidene)-1,2-cyclohexanediamine (1.34 mmol) in acetone solvent was added and stirred overnight. The obtained suspension was filtered and washed with acetone solvent. The dried green powder complex compound was obtained.

Synthesis of Complex Compound (V)

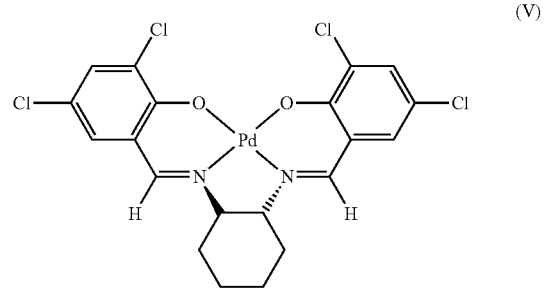

(V)

Palladium acetate (1.34 mmol) was dissolved in hot methanol solvent. Then, (S,S)-(+)-N,N'-bis(3,5-dichlorosalicylidene)-1,2-cyclohexanedi-amine (1.34 mmol) in acetone solvent was added and stirred overnight. The obtained suspension was filtered and washed with acetone solvent. The dried green powder complex compound was obtained.

Synthesis of Complex Compound (VI)

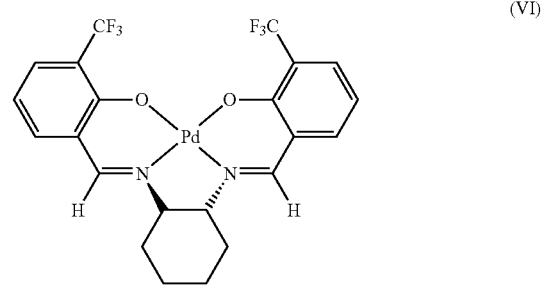

(VI)

Palladium acetate (1.34 mmol) was dissolved in hot methanol solvent. Then, (S,S)-(+)-N,N'-bis(3-trifluoromethylsalicylidene)-1,2-cyclohexanediamine (1.34 mmol) in acetone solvent was added and stirred overnight. The obtained suspension was filtered and washed with acetone solvent. The dried green powder complex compound was obtained.

Synthesis of Complex Compound (VII)

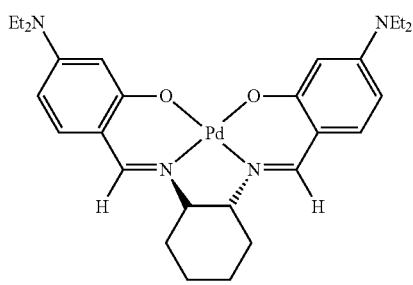

(VII)

Palladium acetate (0.65 mmol) was dissolved in hot methanol solvent. Then, (S,S)-(+)-N,N'-bis(4-diethylamino-salicylidene)-1,2-cyclohexanedi-amine (1.34 mmol) in acetone solvent was added and stirred overnight. The obtained suspension was filtered and washed with acetone solvent. The dried green powder complex compound was obtained.

Production of Unsaturated Carboxylic Acid Salt and its Derivatives from Reaction of Carbon Dioxide and Olefins The complex compounds (II) to (VII) were tested for their catalytic performance in the production of unsaturated carboxylic acid salt and its derivatives for the reaction of carbon dioxide and olefins, wherein dichloro(1,5-cyclooctadiene)palladium(II) ((COD)PdCl$_2$) (Sigma Aldrich) is used as the reference catalyst (REF CAT).

The palladium complex compound (0.1 mmol), ligand (0.11 mmol), base (30 mmol), reducing agent (1-10 mmol), and solvent (30 mL) were added into reactor. Then, olefins (10 bars) and carbon dioxide (20-40 bars) were condensed into reactor. Then, reactor was heated at the temperature of 100-180° C. for 20-25 hours. Then, the temperature was reduced to the room temperature. The obtained mixture was subjected to removal of olefins and carbon dioxide under vacuum. The obtained mixture was used to identify product by NMR spectroscopy, wherein the turn over number (TON) was calculated by the following equation:

The turn over number(TON)=mole of obtained product/mole of catalyst wherein sodium 3-(trimethylsilyl)-2,2,3,3-d4-propionate is used as the internal standard calculated from H$_2$O suppression by NMR spectroscopy.

The following is the testing examples for properties of palladium catalysts produced according to this invention. The methods and instruments used for testing of properties are methods and instruments being used generally and not intended to limit the scope of the invention.

TABLE 1

Catalytic efficiency of 1,3-butadiene and carbon dioxide catalysts of the catalyst compositions according to this invention
Catalyst compositions

| Catalyst | Phosphorous compound | Base | Reducing agent | Additive | Solvent | TON[a] |
|---|---|---|---|---|---|---|
| (COD)PdCl$_2$ | dcpe | Sodium 2-fluorophenolate | Zinc | — | Tetrahydrofuran | 4 |
| (COD)PdCl$_2$ | dcpe | Sodium tert-butoxide | Zinc | — | Tetrahydrofuran | 21 |
| III | dcpe | Sodium 2-fluorophenolate | Zinc | — | Tetrahydrofuran | 2 |
| III | dcpe | Sodium tert-butoxide | Zinc | Triphenylphosphine | N-cyclohexyl-2-pyrrolidone | 32 |
| III | dcpe | Sodium tert-butoxide | Trisodium citrate | Triphenylphosphine | N-cyclohexyl-2-pyrrolidone | 7 |
| II | dcpe | Sodium tert-butoxide | Zinc | — | Tetrahydrofuran | 34 |
| III | dcpe | Sodium tert-butoxide | Zinc | — | Tetrahydrofuran | 35 |
| IV | dcpe | Sodium tert-butoxide | Zinc | — | Tetrahydrofuran | 29 |
| V | dcpe | Sodium tert-butoxide | Zinc | — | Tetrahydrofuran | 35 |
| VI | dcpe | Sodium tert-butoxide | Zinc | — | Tetrahydrofuran | 18 |
| VII | dcpe | Sodium tert-butoxide | Zinc | — | Tetrahydrofuran | 20 |

[a]The turn over number (TON) was recorded as (mole of product)/(mole of palladium catalyst), wherein sodium 3-(trimethylsilyl)-2,2,3,3-d4-propionate is used as the internal standard calculated from H$_2$O suppression by NMR spectroscopy;
(COD)PdCl$_2$ was the reference catalyst (REF CAT); and
dcpe represented bis(dicyclohexylphosphino)ethane).

TABLE 2

Catalytic efficiency of ethylene and carbon dioxide of the catalyst compositions according to this invention
Catalyst compositions

| Catalyst | Phosphorous compound | Base | Reducing agent | Additive | Solvent | TON[a] |
|---|---|---|---|---|---|---|
| III | dcpe | Sodium tert-butoxide | Zinc | tris(2-methoxyphenyl)phosphine | N-cyclohexyl-2-pyrrolidone | 16 |

TABLE 2-continued

Catalytic efficiency of ethylene and carbon dioxide of the catalyst compositions according to this invention
Catalyst compositions

| Catalyst | Phosphorous compound | Base | Reducing agent | Additive | Solvent | TON[a] |
|---|---|---|---|---|---|---|
| III | dcpe | Sodium tert-butoxide | Zinc | tri-p-tolyl phosphite | N-cyclohexyl-2-pyrrolidone | 14 |
| III | dcpe | Sodium tert-butoxide | Zinc | tris(2,4-di-tert-butylphenyl) phosphite | N-cyclohexyl-2-pyrrolidone | 11 |
| III | dcpe | Sodium tert-butoxide | Zinc | Triphenylphosphine | N-cyclohexyl-2-pyrrolidone | 24 |
| III | dcpe | Sodium tert-butoxide | Trisodium citrate | Triphenylphosphine | N-cyclohexyl-2-pyrrolidone | 23 |
| III | dcpe | Sodium tert-butoxide | L-ascorbic acid | Triphenylphosphine | N-cyclohexyl-2-pyrrolidone | 22 |
| III | dcpe | Sodium tert-butoxide | Trisodium citrate | tristearyl phosphite | N-cyclohexyl-2-pyrrolidone | 29 |
| III | dcpe | Sodium tert-butoxide | Trisodium citrate | tri-p-tolyl phosphite | N-cyclohexyl-2-pyrrolidone | 16 |
| II | dcpe | Sodium 2-fluorophenolate | Zinc | — | N-cyclohexyl-2-pyrrolidone | 14 |
| III | dcpe | Sodium 2-fluorophenolate | Zinc | — | N-cyclohexyl-2-pyrrolidone | 16 |
| IV | dcpe | Sodium 2-fluorophenolate | Zinc | — | N-cyclohexyl-2-pyrrolidone | 20 |
| V | dcpe | Sodium 2-fluorophenolate | Zinc | — | N-cyclohexyl-2-pyrrolidone | 21 |
| II | dcpe | Sodium 2-fluorophenolate | Zinc | Triphenylphosphine | N-cyclohexyl-2-pyrrolidone | 21 |
| III | dcpe | Sodium 2-fluorophenolate | Zinc | Triphenylphosphine | N-cyclohexyl-2-pyrrolidone | 19 |
| IV | dcpe | Sodium 2-fluorophenolate | Zinc | Triphenylphosphine | N-cyclohexyl-2-pyrrolidone | 23 |
| V | dcpe | Sodium 2-fluorophenolate | Zinc | Triphenylphosphine | N-cyclohexyl-2-pyrrolidone | 23 |

[a]The turn over number (TON) was recorded as (mole of product)/(mole of palladium catalyst), wherein sodium 3-(trimethylsilyl)-2,2,3,3-d4-propionate is used as the internal standard calculated from $H_2O$ suppression by NMR spectroscopy;
$(COD)PdCl_2$ was the reference catalyst (REF CAT); and
dcpe represented bis(dicyclohexylphosphino)ethane).

Table 1 shows the catalytic efficiency of 1,3-butadiene and carbon dioxide of the catalyst compositions according to this invention. It was found that the palladium catalyst II, III, IV, or V had higher turn over number (TON) than the reference catalyst (REF CAT), which showed that the catalyst compositions according to the invention has high catalytic efficiency in the production process of unsaturated carboxylic acid salt and its derivatives from carbon dioxide and olefins.

Table 2 shows the catalytic efficiency of ethylene and carbon dioxide. Samples in the table aimed to show the application of the catalyst compositions according to the invention, but not intended to limit the scope of the invention by the sample being shown. From the table, the catalyst compositions according to the invention had high turn over number (TON) for catalyzing the production process of the unsaturated carboxylic acid salt and its derivatives from carbon dioxide and ethylene especially when additives were added into the catalyst compositions.

From all above results, it can be said that the catalyst compositions according to the invention has high efficiency in catalyzing the producing process of an unsaturated carboxylic acid salt and its derivatives from carbon dioxide and olefin as aimed in the objective of the invention.

Preferred Embodiment of the Invention

Preferred embodiment of the invention is as provided in the description of the invention.

The invention claimed is:
1. A catalyst composition comprising:
a) a palladium metal complex as shown in structure (I);

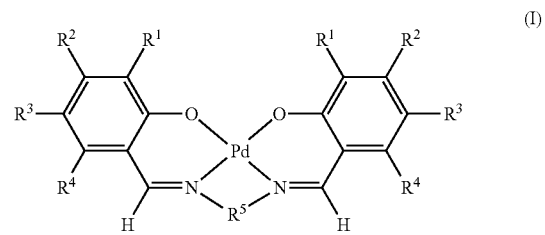

wherein,
$R^1$, $R^2$, $R^3$, and $R^4$ independently represents a group selected from hydrogen atom, halogen atom, alkyl group, alkyl halide group, alkoxy group, amine group, optionally from alkenyl group, alkynyl group, phenyl group, benzyl group, or cylic hydrocarbon group comprising hetero atom;
$R^5$ represents group selected from as alkyl group or phenyl group;
b) a ligand selected from organophosphorus compound;
c) a base selected from sodium tert-butoxide, sodium isopropoxide, sodium 2,6-dimethylphenolate, sodium 2,6-difluorophenolate, sodium 2-methylphenolate, or sodium 2-fluorophenolate); and
d) a reducing agent.
2. The catalyst composition according to claim 1, wherein the palladium metal complex in a) comprising $R^1$, $R^2$, $R^3$, and R⁴ independently selected from hydrogen atom, halogen atom, alkyl halide group, alkyl group having 1-4 carbon atoms, alkoxy group having 1-4 carbon atoms or secondary amine with general formula $NR_2^6$ wherein $R^6$ represents alkyl group having 1-4 carbon atoms.

3. The catalyst composition according to claim 2, wherein the palladium metal complex in a) comprising $R^1$, $R^2$, $R^3$, and $R^4$ independently represents a group selected from hydrogen atom, chlorine atom, tert-butyl group, methoxy group, trifluoromethyl group, or diethylamine group.

4. The catalyst composition according to claim 1, wherein the palladium metal complex in a) comprising $R^5$ represents alkyl group selected from ethylene, 1,2-phenylene, binaphthyl, or 1,2-cyclohexyl.

5. The catalyst composition according to claim 1, wherein the palladium metal complex in a) is selected from the palladium metal complex as shown in structure (II), (III), (IV), (V), (VI), or (VIII);

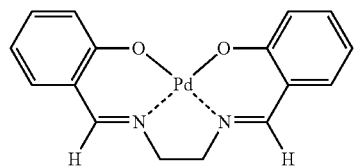
(II)

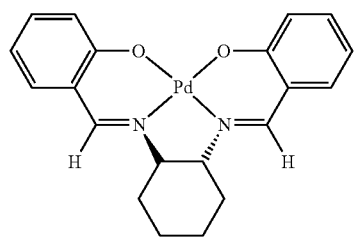
(III)

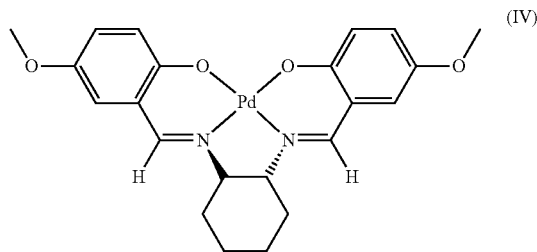
(IV)

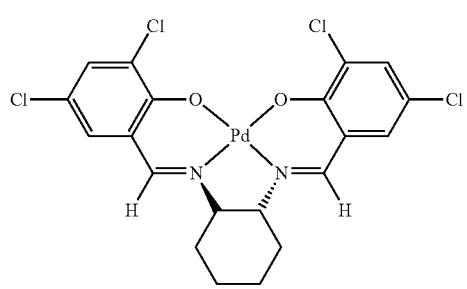
(V)

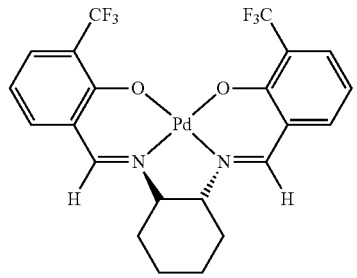
(VI)

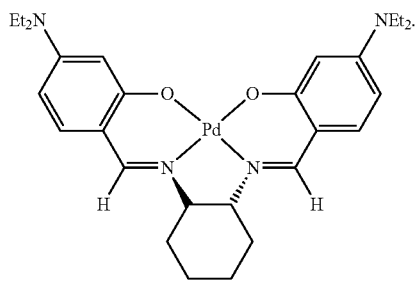
(VII)

6. The catalyst composition according to claim 1, wherein the organophosphorus compound in b) is selected from diphosphine group with a general formula $PR^7_3CH_2CH_2PR^7_3$, wherein $R^7$ is selected from alkyl group, phenyl group, or cycloalkyl group.

7. The catalyst composition according to claim 6, wherein the organophosphorus compound in diphosphine group is selected from bis(dicyclohexylphosphino)ethane, (S,S',R,R')-TangPhos, (R,R)-(−)-2,3-bis(tert-butylmethylphosphino)quinoxaline, (1R,1'R,2S,2'S)-DuanPhos, and (−)-1,2-bis[(2R,5R)-2,5-dimethylphospholano]benzene.

8. The catalyst composition according to claim 1, wherein the organophosphorus compound is bis(dicyclohexylphosphino)ethane.

9. The catalyst composition according to claim 1, wherein the base in c) is sodium tert-butoxide or sodium 2-fluorophenolate.

10. The catalyst composition according to claim 1, wherein the reducing agent in d) is selected from zinc, L-ascorbic acid, or sodium citrate.

11. The catalyst composition according to claim 1, wherein the reducing agent in d) is zinc.

12. The catalyst composition according to claim 1, wherein said catalyst further comprises an additive selected from phosphorus compound with a general formula $PR_3^8$ wherein $R^8$ is selected from alkoxy group, cycloalkyl group, aryl group, or alkoxy aryl group.

13. The catalyst composition according to claim 12, wherein the additive is selected from triphenylphosphine, tricyclohexylphosphine, tris(2-methoxyphenyl)phosphine, tris(4-methoxyphenyl)phosphine, tris(2,6-dimethoxyphenyl)phosphine), tristearyl phosphite, triphenyl phosphite, tris(2,4-di-tert-butylphenyl) phosphite, tri-p-tolyl phosphite, or the mixture thereof.

14. The catalyst composition according to claim 13, wherein the additive is triphenylphosphine or tristearyl phosphite.

15. The catalyst composition according to claim 1, wherein the mole ratio of the catalyst composition comprising:
  a) 1 part of the palladium metal complex;
  b) from 0.5 to 2 parts of ligand;

c) from 50 to 400 parts of base; and d) from 50 to 500 parts of reducing agent.

16. The catalyst composition according to claim 12, wherein said catalyst composition further comprises 0 to 8 parts of additive.

17. A process for reacting carbon dioxide and olefin, wherein said process comprises:
   a) adding of the catalyst composition according to claim 1 in a solvent into a reactor; and
   b) condensing olefin and carbon dioxide with the mixture obtained from step a) in the reactor, then rising the temperature from 100 to 180° C. and heated for 10-25 hours.

18. The process according to claim 17, wherein the mole ratio of olefin to carbon dioxide is from 1 to 2 to 1 to 4.

19. The process according to claim 17, wherein olefin is selected from ethylene, 1,3-butadiene, or 1-hexene.

20. The process according to claim 17, wherein the solvent in a) is selected from tetrahydrofuran, anisole, N-cyclohexyl-2-pyrrolidone, phenyl butyl ether, dibutyl glycol ether, dibutyl ether, N,N-dimethylacetamide, N,N-dimethylformamide, N,N-dibutylformamide, or the mixture thereof.

21. The process according to claim 20, wherein the solvent is tetrahydrofuran or N-cyclohexyl-2-pyrrolidone.

22. The process according to claim 17, wherein the temperature in step b) is from 130 to 150° C. and heated for 15-25 hours.

* * * * *